United States Patent [19]

Berneth et al.

[11] Patent Number: 4,968,797
[45] Date of Patent: Nov. 6, 1990

[54] CHROMOGENIC 4,4-DIARYLDIHYDROQUINAZOLONES

[75] Inventors: Horst Berneth, Leverkusen; Alfred Brack, Odenthal; Karlheinrich Meisel, Leverkusen, all of Fed. Rep. of Germany

[73] Assignee: Bayer Aktiengesellschaft, Leverkusen, Fed. Rep. of Germany

[21] Appl. No.: 115,137

[22] Filed: Oct. 30, 1987

Related U.S. Application Data

[62] Division of Ser. No. 789,686, Oct. 21, 1985, Pat. No. 4,754,034.

[30] Foreign Application Priority Data

Oct. 26, 1984 [DE] Fed. Rep. of Germany ....... 3439282

[51] Int. Cl.$^5$ ............................................ C07D 239/80
[52] U.S. Cl. .................................. 544/284; 427/146;
544/73; 544/74; 544/80; 544/95; 544/101;
544/116; 544/182; 544/195; 544/212; 544/214;
544/219; 544/232; 544/244; 544/247; 544/250;
544/251; 544/286
[58] Field of Search ............... 544/284, 116, 195, 212, 544/232, 244, 247, 250, 286

[56] References Cited

U.S. PATENT DOCUMENTS 4,625,027 11/1986 Zink et al. ............................ 544/284
4,677,109 6/1987 Bernáth et al. ...................... 544/284
4,695,633 9/1987 Berneth et al. ...................... 544/284

*Primary Examiner*—Richard L. Raymond
*Assistant Examiner*—James H. Turnipseed
*Attorney, Agent, or Firm*—Sprung Horn Kramer & Woods

[57] ABSTRACT

4,4-diaryldihydroquinazolones of the formula

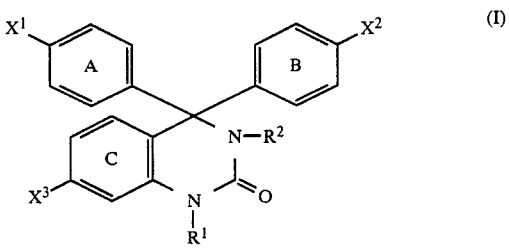

wherein $X^1$, $X^2$ and $X^3$, independently of one another, denote hydrogen, halogen, alkyl, aryl, alkanoylamino, aroylamino, heteryl, $NY^1Y^2$, $OY^3$ or $SY^3$, at least one of the radicals $X^1$, $X^2$ or $X^3$ standing for $NY^1Y^2$, $OY^3$ or $SY^3$, $R^1$ denotes hydrogen, alkyl, cycloalkyl, aralkyl, aryl or the members of a bridge to the o-carbon of ring C, $R^2$ denotes a radical of an acid, $Y^1$, $Y^2$ and $Y^3$, independently of one another, denote hydrogen, alkyl, cycloalkyl, aralkyl aryl or heteryl or the remaining members of a 5- or 6-membered ring which reaches to one of the o-position benzene C atoms and may contain further hetero atoms or $Y^1+Y^2$ denote the remaining members of a 5- or 6-membered ring which may contain further hetero atoms and the rings A, B and C and the radicals mentioned can in turn carry nonionic substituents customary in dye-stuff chemistry, find utility in pressure-copyable thermoreactive and electrochromic recording materials.

3 Claims, No Drawings

CHROMOGENIC 4,4-DIARYLDIHYDROQUINAZOLONES

This is a division of application Ser. No. 789,686, filed Oct. 21, 1985, now U.S. Pat. No. 4,754,034.

The invention relates to chromogenic 4,4-diaryldihydroquinazolones of the formula

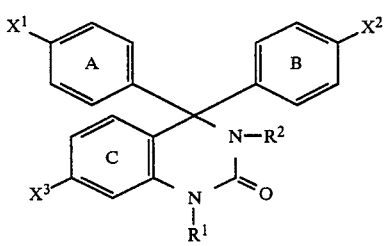

wherein
$X^1$, $X^2$ and $X^3$, independently of one another, denote hydrogen, halogen, alkyl, aryl, alkanoylamino, aroylamino, heteryl, $NY^1Y^2$, $OY^3$ or $SY^3$, at least one of the radicals $X^1$, $X^2$ or $X^3$ standing for $NY^1Y^2$, $OY^3$ or $SY^3$, $R^1$ denotes hydrogen, alkyl, cycloalkyl, aralkyl, aryl or the members of a bridge to the o-carbon of ring C, $R^2$ denotes a radical of an acid, $Y^1$, $Y^2$ and $Y^3$, independently of one another, denote hydrogen, alkyl, cycloalkyl, aralkyl, aryl or heteryl or the remaining members of a 5- or 6-membered ring which reaches to one of the o-position benzene C atoms and may contain further hetero atoms or $Y^1 + Y^2$ denote the remaining members of a 5- or 6-membered ring which may contain further hetero atoms and the rings A, B and C and the radicals mentioned can in turn carry nonionic substituents customary in dyestuff chemistry, to their preparation and to their use in pressure-copyable, thermoreactive and electrochromic recording materials.

Examples of nonionic substituents customary in dyestuff chemistry are: halogen, hydroxyl, alkoxy, aryloxy, aralkoxy, hetaryloxy, aryl, heteryl, alkylmercapto, arylmercapto, aralkylmercapto, alkylsulphonyl, cyano, carbamoyl, alkoxycarbonyl, amino which can be substituted by 1 or 2 alkyl, aryl or aralkyl groups, or its substituents can be cyclised, alkenyloxy, alkylcarbonyloxy and arylcarbonyloxy and as substituents on the rings also alkyl, aralkyl, nitro, alkenyl or arylvinyl.

Preferably alkyl stands for $C_1$-$C_{30}$-alkyl, in particular for $C_1$-$C_{12}$-alkyl and especially for $C_1$-$C_4$-alkyl, and alkenyl stands for $C_2$-$C_5$-alkenyl.

Halogen is to be understood as meaning in particular chlorine and bromine.

The alkyl radicals and the alkyl radicals in alkoxy, alkylthio, dialkylamino, alkanoylamino, alkylsulphonyl and alkoxycarbonyl groups can be branched and substituted, for example, by fluorine, chlorine, $C_1$- to $C_4$-alkoxy, cyano or $C_1$-$C_4$-alkoxycarbonyl; particular examples are methyl, ethyl, propyl, 2-propyl, 2,2-dimethylpropyl, 2-butyl, 1-hexyl, 1-octyl, 1-dodecyl, 1-tetradecyl, 1-hexadecyl, 1-octadecyl, 2-bornylmethyl, 2-chloroethyl, 2-cyanoethyl, 2-methoxyethyl, 2-ethoxycarbonylethyl and trifluoromethyl.

In particular cycloalkyl is to be understood as meaning cyclohexyl, aryl is to be understood as meaning phenyl and naphthyl, aralkyl is to be understood as meaning benzyl and phenethyl, heteryl is to be understood as meaning pyridyl, pyrimidyl, pyrazinyl, triazinyl, indolyl, imidazolyl, oxazolyl, thiazolyl, triazolyl, thiadiazolyl or tetrazolyl, each of which can be benzofused, and heteralkyl is to be understood as meaning the stated rings or ring systems which can be bonded to nitrogen by methylene or ethylene. The rings can be substituted by nonionic substituents, in particular by $C_1$-$C_4$-alkyl, $C_1$-$C_4$-alkoxy, cyano, nitro or halogen.

The phenyl and naphthyl radicals and the radicals in benzyl or benzoylamino groups can carry up to 3 identical or different radicals.

Particular examples of substituted phenyl radicals are 2-, 3- or 4-tolyl, 2-, 3- or 4-anisyl, 2-, 3- or 4-chlorophenyl, 2-, 3- or 4-nitrophenyl, 2-, 3- or 4-cyanophenyl, 2-, 3- or 4-ethoxycarbonylphenyl, 2-, 3- or 4-methoxysulphonylphenyl, 2-, 3- or 4-trifluoromethylphenyl, 2,3-dinitrophenyl, 3,4-dimethylphenyl, 2-chloro-4-nitrophenyl, 3-chloro-4-nitrophenyl, 5-chloro-2-methyl-4-nitrophenyl, 4-chloro-3-methylphenyl, 3-chloro-4-methoxyphenyl, 3-chloro-4-trifluoromethylphenyl, 3,4-dicyanophenyl, 2,5-dichloro-4-cyanophenyl and 2-methyl-1-naphthyl.

The heterocyclic radicals can carry up to 4 identical or different radicals. Particular examples of substituted heterocyclic radicals are 2-methyl-4-pyridyl, 4-nitro-2-pyridyl, 4-phenylthiazol-2-yl, 5-methylbenzoxazolyl, 5tert.-butyl-benzothiazolyl, 1,2-dimethylindol-3- or -5-yl and 2,2,6,6-tetramethylpiperidin-4-yl.

Preferred alkanoyl are acetyl and propionyl, and preferred aroyl is benzoyl.

The radical $R^2$ of an acid is to be understood as meaning radicals of organic or inorganic acids of the formula $$R^2OH \qquad (II)$$

Of the compounds of the formula I, a special mention should go to the compounds of the formula

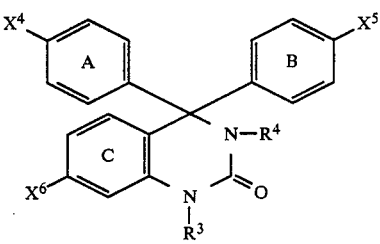

wherein
one of the radicals $X^4$, $X^5$ or $X^6$ stands for $NY^4Y^5$ and the others, independently of each other, denote hydrogen, halogen, $C_1$-$C_{18}$-alkyl, optionally chlorine- and/or $C_1$ to $C_{12}$-alkyl-substituted phenyl, $C_1$- to $C_{12}$-alkanoylamino, optionally chlorine- and/or $C_1$- to $C_{12}$-alkyl-substituted benzoylamino, optionally $C_1$- to $C_4$-alkyl-, $C_1$- to $C_4$-alkoxy-, chlorine- or phenyl-substituted indolyl or piperidyl radicals, $NY^4Y^5$, $OY^6$ or $SY^6$, $R^3$ denotes hydrogen, $C_1$- to $C_{18}$-alkyl, cyclohexyl or optionally chlorine- and/or $C_1$- to $C_{18}$-alkyl-substituted benzyl or phenyl radicals, $R^4$ denotes a radical of the formulae

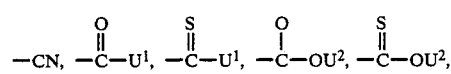

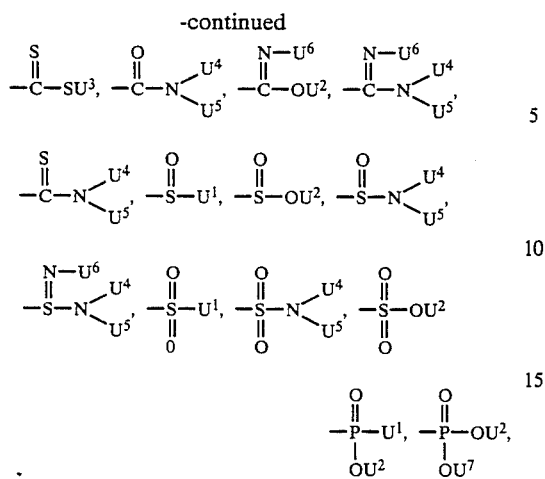

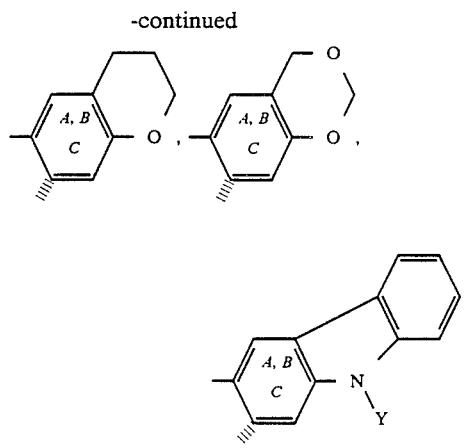

$U^1$ to $U^7$ denote hydrogen, optionally fluorine-, chlorine-, cyano-, $C_1$- to $C_4$-alkoxycarbonyl- and/or $C_1$- to $C_4$-alkoxy-carrying $C_1$- to $C_{30}$-alkyl, optionally chlorine- and/or $C_1$- to $C_{18}$-alkyl-carrying cyclohexyl, optionally chlorine-, bromine-, nitro-, $C_1$- to $C_{18}$-alkyl, $C_1$- to $C_{18}$-alkoxy, $C_1$- to $C_{18}$-alkylthio, $C_1$- to $C_{18}$-monoalkylamino- or -dialkylamino-, $C_1$- to $C_{18}$-alkylsulphonyl-, cyano- and/or $C_1$- to $C_{18}$-alkoxycarbonyl-carrying phenyl, benzyl, naphthyl, picolyl, pyridyl, quinolyl, pyrimidyl, pyrazinyl, triazinyl, triazolyl, thiadiazolyl, tetrazolyl, indolyl, optionally benzofused imidazole, oxazole or thiazole radicals, $Y^4$, $Y^5$ and $Y^6$, independently of one another, denote hydrogen, optionally chlorine-, cyano-, $C_1$- to $C_4$-alkoxycarbonyl- or $C_1$- to $C_4$-alkoxy-substituted $C_1$- to $C_{18}$-alkyl, cyclohexyl or phenyl or benzyl, each of which can be substituted by chlorine, $C_1$- to $C_{12}$-alkyl or $C_1$- to $C_{12}$-alkoxy, $C_1$- to $C_4$-alkyl-substituted piperidyl or members which, together with N or O to which they are bonded and one of the rings A, B or C, are necessary for completing a ring system of the following formulae wherein the broken line denotes the further fusion in the case of ring C, Y stands for hydrogen, $C_1$- to $C_{18}$-alkyl which can be substituted by chlorine, cyano, $C_1$- to $C_4$-alkoxycarbonyl or $C_1$- to $C_4$-alkoxy, cyclohexyl, phenyl or benzyl, each of which can be substituted by chlorine, $C_1$- to $C_{12}$-alkyl or $C_1$- to $C_{12}$-alkoxy, the saturated ring moiety can carry up to 4 radicals from the group comprising chlorine, $C_1$- to $C_4$-alkyl, $C_1$- to $C_4$-alkoxy or phenyl, the rings A, B and C can be substituted by chlorine, $C_1$- to $C_4$-alkyl, $C_1$- to $C_4$-alkoxy, optionally chlorine-, $C_1$- to $C_4$-alkyl or $C_1$- to $C_4$-alkoxy-substituted phenoxy or phenylamino and/or $C_1$- to $C_4$-alkanoylamino, or $NY^4Y^5$ denotes an optionally chlorine-, $C_1$- to $C_4$-alkyl- or aryl-, in particular phenyl-, substituted pyrrolo, pyrrolidino, piperidino, pipecolino, morpholino, pyrazolo or pyrazolino radical.

Examples of radicals substituted in the saturated ring are:

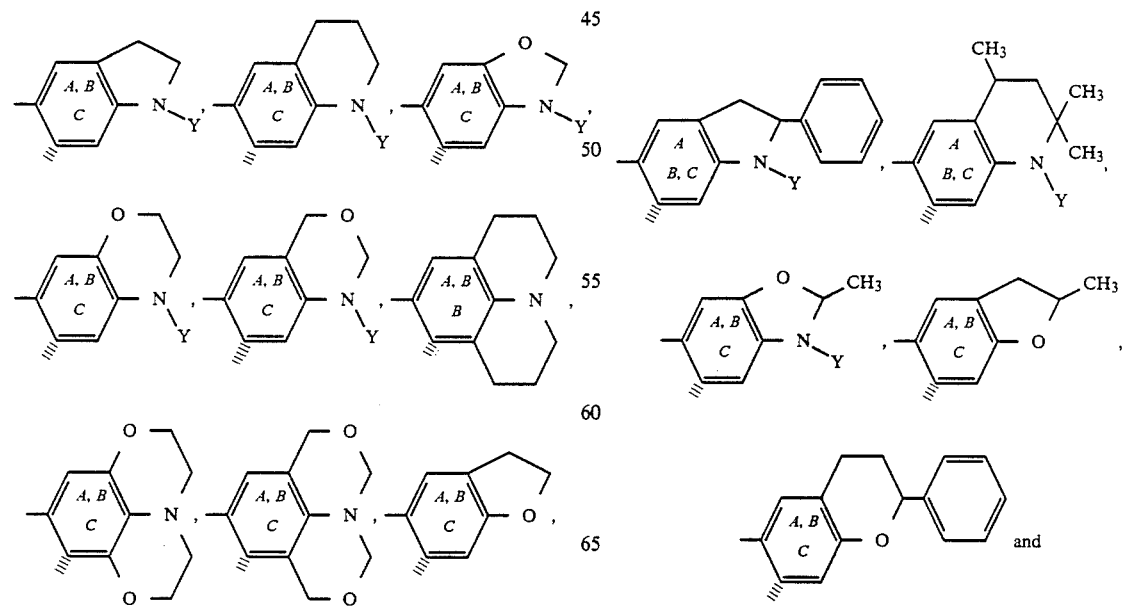

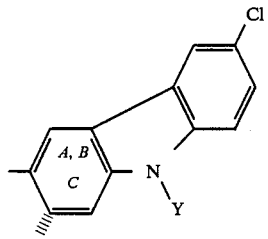

In preferred compounds of the formula

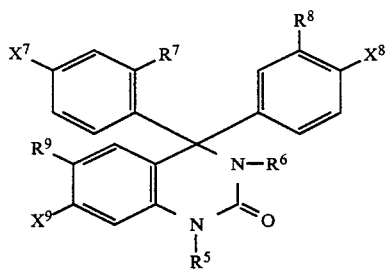

wherein
one of the radicals $X^7$, $X^8$ and $X^9$ stands for $NY^7Y^8$ and the others, independently of each other denote hydrogen, chlorine, bromine, $C_1$- to $C_{18}$-alkyl, optionally chlorine- and/or $C_1$- to $C_4$-alkyl-substituted phenyl, $C_1$- to $C_4$-alkanoylamino, optionally chlorine- and/or $C_1$- to $C_4$-alkyl-substituted benzoylamino, optionally methyl-, ethyl-, methoxy-, chlorine- or phenyl-substituted indolyl or piperidyl radicals, $NY^7Y^8$, $OY^9$ or $SY^9$, $R^5$ denotes hydrogen, $C_1$- to $C_4$-alkyl, cyclohexyl or phenyl, $R^6$ denotes

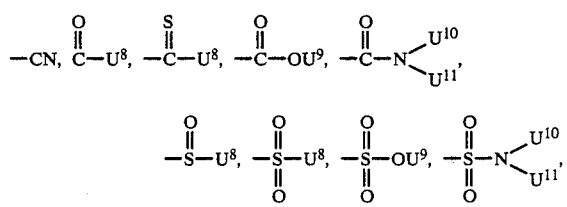

$U^8$–$U^{11}$ denote hydrogen, optionally fluorine-, chlorine- or $C_1$- to $C_4$-alkoxy-carrying $C_1$- to $C_{18}$-alkyl, cyclohexyl, optionally chlorine- and/or $C_1$- to $C_8$-alkyl-carrying benzyl, optionally chlorine-, bromine-, nitro-, $C_1$- to $C_{18}$-alkyl, $C_1$- to $C_{18}$-alkoxy, $C_1$- to $C_{18}$-alkylthio, $C_1$- to $C_{18}$-dialkylamino, $C_1$- to $C_{18}$-alkylsulphonyl, cyano- and/or $C_1$- to $C_{18}$-alkoxycarbonyl-carrying phenyl, naphthyl, picolyl, pyridyl, quinolyl, pyrimidyl, pyrazinyl, triazinyl, triazolyl, thiadiazolyl, tetrazolyl, indolyl, optionally benzo-fused imidazole, oxazole or thiazole radicals, $R^7$, $R^8$ and $R^9$, independently of one another, denote hydrogen, chlorine, bromine, $C_1$- to $C_4$-alkyl, $C_1$- to $C_4$-alkoxy, $C_1$- to $C_4$-alkylthio, amino or $C_1$- to $C_4$-alkylamino, $C_1$- to $C_4$-monoalkylamino or -dialkylamino, optionally methyl-, methoxy-, ethoxy- or chlorine-substituted anilino or N-$C_1$- to $C_4$-alkylanilino, $Y^7$, $Y^8$ and $Y^9$, independently of one another, denote hydrogen, chlorine-, cyano-, methoxycarbonyl-, hydroxyl-, methoxy- or ethoxy-substituted $C_1$- to $C_{18}$-alkyl, cyclohexyl, benzyl or phenyl, each of which can be substituted by chlorine, methyl or methoxy, 2,2,6,6-tetramethylpiperidinyl-4-yl or 1,2,2,6,6-pentamethylpiperidinyl-4-yl or $Y^7$, $Y^8$ and $Y^9$ stand for the members which lead to the ring systems listed in the context of the formula III under $Y^4$, $Y^5$ and $Y^6$ or $NY^7Y^8$ stands for a $C_1$- to $C_4$-alkyl- and/or phenyl-substituted pyrrolidino, piperidino, morpholino or pyrazolino radical.

A very particular mention should go to 4,4-diaryl-dihydroquinoazolones of the formula

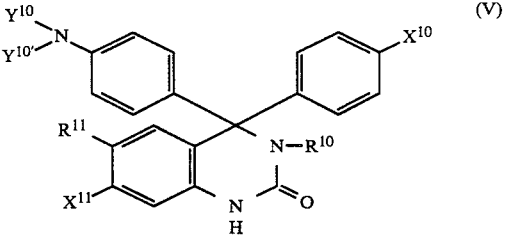

wherein
$R^{10}$ denotes cyano, acetyl, trifluoroacetyl, propionyl, butanoyl, pivaloyl, hexanoyl, octanoyl, 2-ethylhexanoyl, decanoyl, dodecanoyl, tetradecanoyl, hexadecanoyl, octadecanoyl, cyclohexylcarbonyl, phenylacetyl, benzoyl, chlorobenzoyl, toluoyl, tert.-butylbenzoyl, hexylbenzoyl, dodecylbenzoyl, anisoyl, nitrobenzoyl, cyanobenzoyl, trifluoromethylbenzoyl, methoxycarbonylbenzoyl, hexoxycarbonylbenzoyl, dodecoxycarbonylbenzoyl, methoxysulphonylbenzoyl, methylsulphonylbenzoyl, dinitrobenzoyl, chloronitrobenzoyl, dichlorobenzoyl, chloroethylthiobenzoyl, naphthoyl, pyridoyl, quinoloyl, 2-, 3- or 5-indolyl, 5-benzoxazolyl, pyridylacetyl, methoxycarbonyl, ethoxycarbonyl, propoxycarbonyl, butoxycarbonyl, hexoxycarbonyl, dodecoxycarbonyl, octadecoxycarbonyl, phenoxycarbonyl, dimethylaminocarbonyl, diethylaminocarbonyl, phenylaminocarbonyl, methylphenylaminocarbonyl, dimethylaminosulphonyl, diethylaminosulphonyl, phenylaminosulphonyl, methylphenylaminosulphonyl, methanesulphonyl, ethanesulphonyl, trifluoromethanesulphonyl, nonafluorobutanesulphonyl, heptadecafluorooctanesulphonyl, methanesulphinyl, octanesulphinyl, benzenesulphonyl, chlorobenzenesulphonyl, dichlorobenzenesulphonyl, nitrobenzenesulphonyl, chloronitrobenzenesulphonyl, trichloronitrobenzenesulphonyl, toluenesulphonyl, chloromethylbenzenesulphonyl, methylnitrobenzenesulphonyl, dimethylbenzenesulphonyl, methyldinitrobenzenesulphonyl, methoxybenzenesulphonyl, dichloromethoxybenzenesulphonyl, methoxynitrobenzenesulphonyl, naphthalenesulphonyl, biphenylsulphonyl, cyanobiphenylsulphonyl, benzenesulphinyl, chlorobenzenesulphinyl, methylbenzenesulphinyl, benzoxazole-5-sulphonyl, $R^{11}$ denotes hydrogen, chlorine, methyl or methoxy, $X^{10}$ denotes $NY^{11}Y^{11'}$, hydrogen, chlorine, $C_1$–$C_4$-alkyl, methoxy, ethoxy, propoxy, butoxy, hexoxy, dodecoxy, octadecoxy, benzyloxy, methylthio or ethylthio, $X^{11}$ denotes hydrogen, chlorine $C_1$- to $C_4$-alkyl, benzyl, methoxy, ethoxy, propoxy, butoxy, hexoxy, dodecoxy, octadecoxy, benzyloxy, methylthio, ethylthio, acetylamino, propionylamino, butanoylamino, decanoylamino, octadecanoylamino, benzoylamino, NHCONHR$^{10}$ or NY$^{12}$Y$^{12'}$, Y$^{10}$–Y$^{12}$ denote methyl, ethyl, propyl, butyl, hexyl, dodecyl, octadecyl, cyanoethyl, methoxyethyl, methoxycarbonylethyl, benzyl, phenyl, 4-tolyl, 4-chlorophenyl, 4-anisyl, 4-ethoxyphenyl, 4-cyanophenyl, Y$^{10'}$–Y$^{12'}$ denote hydrogen or the meaning of Y$^{10}$–Y$^{12}$ or NY$^{10}$Y$^{10'}$, NY$^{11}$Y$^{11'}$ or NY$^{12}$Y$^{12'}$ denotes

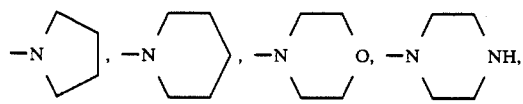

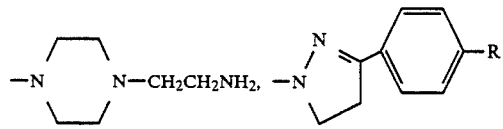

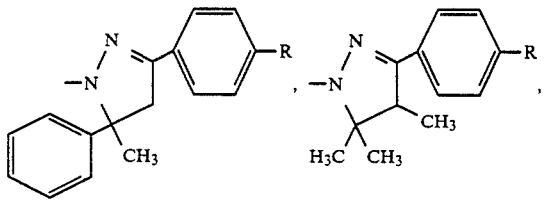

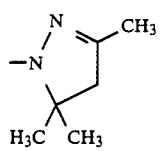

and

R denotes hydrogen, chlorine, methyl, methoxy, ethoxy or cyano.

The invention also relates to leuco compounds of the formula

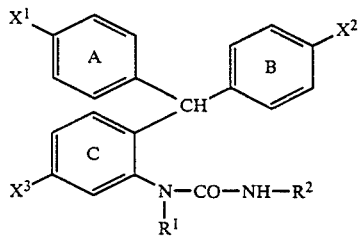
(VI)

wherein

R$^1$, R$^2$, X$^1$, X$^2$, X$^3$, A, B and C have the meaning indicated in the context of the formula I and specified as preferable in the case of the formulae (III)–(V).

The invention also relates to a process for preparing a 4,4-diaryl-dihydroquinazolone of the formula (I), characterised in that a urea compound of the formula

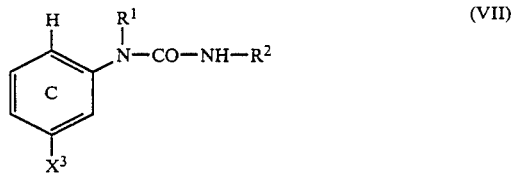
(VII)

is reacted with a ketone of the formula

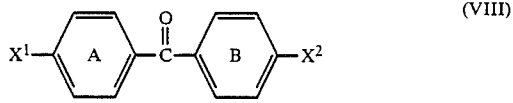
(VIII)

wherein

X$^1$, X$^2$, X$^3$, R$^1$, R$^2$, A, B and C have the above-mentioned meaning.

The compounds (VII) are in particular those in which X$^3$ is an electron donor substituent, such as NY$^1$Y$^2$, OY$^3$ or SY$^3$, wherein Y$^1$ to Y$^3$ have the abovementioned meaning and the ring C is not deactivated by strong electron acceptor substituents such as, for example, nitro, cyano or alkoxycarbonyl.

The reaction is customarily effected with water-eliminating reagents in the absence or presence of solvents which are inert under these conditions, at temperatures between 0° C. and the boiling point of the medium in question. Subsequently and possibly after removal of the inert solvent, the reaction mixture is discharged on to, for example, water or an alcohol. By raising the pH with, for example, alkali or alkaline earth metal hydroxides, carbonates, hydrogencarbonates, ammonia or amines until the colour of this mixture has disappeared it is possible to obtain the 4,4-diaryldihydroquinazolones of the formula I. With this reaction it can be necessary to apply heat for some time to eliminate the water from any carbinol bases formed or to treat the primarily obtained impure product in solvents such as alcohols—for example methanol, ethanol, 2-propanol or butanol; nitriles—for example acetonitrile; ketones—for example acetone or 2-butanone; or esters—for example ethyl acetate or butyl acetate, for some time at temperatures between room temperature and the boiling point of the medium in question.

Examples of water-eliminating reagents are phosphorus oxychloride, phosphorus pentachloride, diphosphorus pentoxide, phosgene, phosphorus trichloride, phosphorus tribromide, sulphuryl chloride, thionyl chloride, oxalyl chloride or mixtures thereof. Preference is given to the use of phosphorus oxychloride and phosphorus oxychloride/diphosphorus pentoxide.

Examples of suitable inert solvents are toluene, chlorobenzene, dichlorobenzene, nitrobenzene and chlorinated aliphatic hydrocarbons, such as 1,2-dichloroethane.

The 4,4-diaryldihydroquinazolones of the formula (I) can also be prepared by oxidation of leuco compounds of the formula

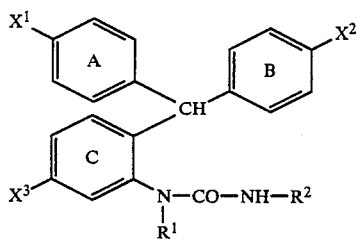

(VI)

wherein $X^1$, $X^2$, Xhu 3, $R^1$, A, B and C have the above-mentioned meaning.

This oxidation can be effected in known manner by means of higher-valent metal compounds, such as $PbO_2$, $MnO_2$, permanganates, $CrO_3$, chromates, dichromates, $NiO_2$ or $K_3[Fe(CN)_6]$, or by means of quinones, such as chloroanil, tetrachloro-o-quinone or dichlorodicyanoquinone, or using some other method described in the literature, such as, for example, by means of oxygen, air, perborates or hydrogen peroxide.

The working-up, isolation and possible aftertreatment is carried out analogously to the procedure described above.

The oxidation by means of higher-valent metal compounds is customarily carried out in an acid medium or in organic solvents, such as alcohols—for example ethanol, isopropanol or ethylene glycol monomethyl ether; ketones—for example acetone, butanone or methyl isopropyl ketone or polar aprotic solvents, for example N-methylpyrrolidone, γ-butyrolactone, acetonitrile, dimethyl sulphoxide or sulpholane or in mixtures of such solvents with acids, at temperatures between 0° C. and 60° C., preferably 10–40° C.

Examples of suitable acids are hydrochloric acid, sulphuric acid, phosphoric acid, acetic acid, propionic acid or mixtures thereof and/or mixtures with water. A preferred mixture is hydrochloric acid, acetic acid and water.

The oxidation by means of quinones is customarily carried out in organic solvents, such as alcohols—for example methanol, ethanol or isopropanol; ketones—for example acetone or butanone; esters, for example ethyl acetate or butyl acetate; carboxylic acids—for example acetic acid or propionic acid, or polar aprotic solvents, such as N-methylpyrrolidone, dimethylformamide, γ-butyrolactone, acetonitrile, sulpholane or in mixtures thereof, at temperatures between 0° C. and the boiling point of the medium, preferably 20–70° C.

The 4,4-diaryldihydroquinazolones of the formula (I) are normally colourless or at most slightly coloured.

On bringing the colour formers into contact with a preferably acid developer, that is to say an electron acceptor, the results are strong blue, greenish blue, green, violet or red colours which have excellent sublimation and light fastness properties. Through the use of mixtures thereof it is possible to obtain navy, grey or black colours.

They are also useful when mixed with one or more other known colour formers, for example 3,3-bis-(aminophenyl)-phthalides, 3,3-bis-(indolyl)-phthalides, 3-aminofluoranes, 2,6-diaminofluoranes, leucoauramines, spiropyrans, spirodipyrans, chromenoindoles, phenoxazines, phenothiazines, carbazolylmethanes or further triarylmethane leuco dyestuffs in order to produce green, violet, blue, navy, grey or black colours.

The 4,4-diaryldihydroquinazolones of the formula (I) exhibit high colour intensity and light fastness not only on phenolic substrates but also in particular on activated clays. They are suitable in particular for use as colour formers in a heat-sensitive or pressure-sensitive recording material, including copying material. Their rate of development varies in dependence upon the substituents. In general they have a high rate of development together with a reduced sensitivity to unintentional premature development.

A pressure-sensitive material consists for example of at least 1 pair of sheets which contain at least one colour former of the formula I in the form of a solution or dispersion in a non-volatile organic solvent and an electron acceptor as a developer.

Typical examples of such developers are inorganic substances such as clays, metal salts or oxides and organic polymers such as phenolic resins.

The developers can in addition also be used in mixtures with other pigments having little or no inherent reactivity.

At the dots where the colour former comes into contact with the electron acceptor a coloured mark is produced. To prevent premature activation of the colour formers present in the pressure-sensitive recording material, the colour formers are generally separated from the electron acceptor. An advantageous way of achieving this separation is to incorporate the colour formers in foam-like, spongelike or honeycomblike structures. Preferably the colour formers are enclosed in microcapsules which are generally breakable by the application of pressure. Processes for preparing such microcapsules are known.

Examples of suitable non-volatile solvents are partially hydrogenated terphenyl, alkylated naphthalenes and dibutyl phthalate.

Preference is given to an arrangement in which the encapsulated colour former is present in the form of a layer on the back of a transfer sheet and the electron acceptor is present in the form of a layer on the front of a receiving sheet.

In another arrangement of the constituents, the microcapsules containing the colour former and the developer are present within or on the same sheet in the form of one or more individual layers or in the paper pulp.

The compounds of the formula I can preferably also be used as colour formers in a thermoreactive recording material. The latter generally contains at least one carrier, a colour former, an electron acceptor and if desired also a binder.

Thermoreactive recording systems encompass, for example heat-sensitive recording and copying materials and papers. These systems are used for example for recording signals, for example in electronic computers, teleprinters, telewriters or in recording appliances and measuring instruments, such as, for example, electrocardiographs. The production of an image (the process of marking) can also be carried out manually by means of a heated nib. A further means of producing markings by means of heat is a laser beam.

The structure of the thermoreactive recording material can be such that the colour former is dissolved or dispersed in a binder layer and, in a second layer, the developer is dissolved or dispersed in the binder. Another possibility is that both the colour former and the developer are dispersed in one and the same layer. The binder is softened by means of heat in specific areas and it is in these areas to which heat is applied that the colour former comes into contact with the electron acceptor, and the desired colour develops at once.

Suitable developers are the same electron acceptors as are used in pressure-sensitive papers, preferably phenolic compounds, as described for example in German Patent No. 1,251,348, and also boric acid and organic, preferably aliphatic, dicarboxylic acids.

The binders used to prepare the thermoreactive recording material are preferably fusable and film-forming. Such binders are normally water-soluble, whereas the 4,4-diaryldihydroquinazolones and the developer are sparingly soluble or insoluble in water. The binder should be capable of dispersing and fixing the colour former and the developer at room temperature.

Under the action of heat the binder softens or melts, so that the colour former comes into contact with the developer and a colour can form. Examples of binders which are water-soluble or at least water-swellable are hydrophilic polymers, such as polyvinyl alcohol, polyacrylic acid, hydroxyethylcellulose, methylcellulose, carboxymethylcellulose, polyacrylamide, polyvinylpyrrolidone, gelatin and starch.

The thermoreactive layers can contain further additives: for improving the whiteness, for facilitating the printing of the papers, for preventing the adhesion of the heated nib and for colour formation only within a limited temperature range.

The leuco compounds of the formula VI can for example be incorporated into customary pressure- or thermoreactive papers as slow-developing colour formers. There, owing to their good light fastness, they act as cocomponents for fast-developing but less light-fast colour formers, for example crystal violet lactone. In this way the light fastness of the recording is improved.

The leuco compounds of the formula VI are also suitable for oxidatively developing pressure- or thermoreactive recording materials. In this case the colour former or the electron acceptor has added to it a suitable oxidising agent, while the subsequent processing of layers is similar to that in the case of customary thermo- or pressure-sensitive recording materials. By contact with the oxidising agent the leuco compound is oxidised to the dyestuff and in this way produces a coloured marking.

The processes and preparations described are known for example from U.S. Pat. Nos. 2,948,753, 3,096,189 and 3,193,404 and German Offenlegungsschriften 2,555,080 and 2,700,937.

The 4,4'-diaryldihydroquinazolones of the formula I and the dyestuffs formed therefrom by ring opening are suitable for dyeing polyacrylonitrile, mordanted cotton and other acid-modified fibres, fabrics and powders.

EXAMPLE 1

27.0 g of Michler's hydrol and 31.8 g of N-(3-dimethylaminophenyl)-N'-(4-chlorobenzoyl)-urea are refluxed under nitrogen in 150 ml of ethanol and 3.5 ml of glacial acetic acid for 30 min. Cooling down is followed by filtering with suction, washing with methanol and drying: 50.0 g (88% of theory) of a greyish beige powder having a melting point of 231–233° C. and the formula

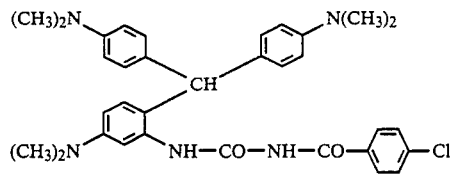

28.5 g of this leuco compound in 100 ml of 80% strength acetic acid and 15 g of concentrated hydrochloric acid have added to them at 5° C. 38 ml of a 31% strength aqueous lead dioxide suspension. The temperature rises to 32° C. After 7 minutes 35 ml of 20% strength sulphuric acid are added, the lead sulphate is filtered off, and the deep blue filtrate, after dilution with 160 ml of methanol, is added dropwise to a solution of 80 g of sodium hydroxide in 800 ml of ice-water. The blue precipitate is filtered off with suction and is washed with water until neutral. While still moist it is added to 100 ml of ethanol. The pale beige suspension is stirred for 2 hours, is filtered off with suction and is again added while still moist to 80 ml of ethanol. This is followed by stirring at 60–70° C. for 2 h, filtering off with suction after cooling down, washing with ethanol and drying in vacuo: 20.5 g (72% of theory) of a pale beige powder having a melting point of 261–263° C. (decomposition; from DMF) and the formula

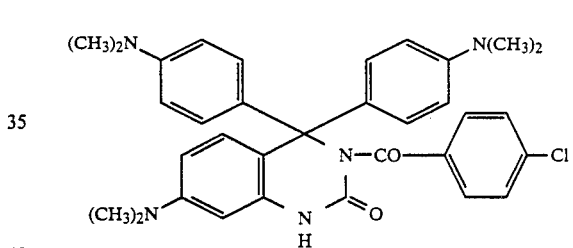

A solution in glacial acetic acid turns blue with $\lambda_{max} = 608$ nm. A deep blue colour develops on acid clay and in thermoprinting with bisphenol A.

The compound used as the starting material, namely N-(3-dimethylamino)-N'-(4-chlorobenzoyl)-urea, is prepared as follows:

36.4 g of 4-chlorobenzoyl isocyanate are added dropwise to 27.2 g of 3-dimethylaminoaniline in 300 ml of anhydrous toluene. Heating brings down a dense precipitate, which is filtered off with suction after 2 h, is washed with toluene and is dried: 59.6 g (94% of theory) of a colourless crystalline powder. This powder is boiled in 250 ml of ethanol for 1 h and after cooling down filtered off with suction, washed and dried: 34.4 g (54% of theory) of a colourless crystalline powder having a melting point of 214.5–215-5° C. and the formula

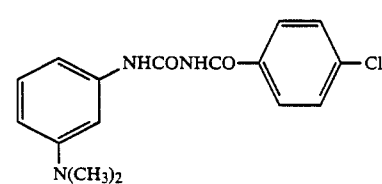

EXAMPLE 2

13.5 g of Michler's hydrol and 22.25 g of N-(3-dimethylaminophenyl)-N'-stearoylurea are refluxed under nitrogen in 70 ml of ethanol and 3 ml of glacial acetic acid and 0.5 ml of concentrated hydrochloric acid for 3.5 h. Cooling down is followed by filtering with suction, washing with ethanol and drying in vacuo. The result obtained is 26.9 g (77%) of a beige powder having a melting point of 123° C. and the formula

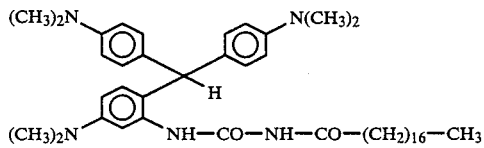

24.4 g of this leuco compound in 50 ml of dimethylformamide are added, at 50° C., 8.61 g of chloroanil. 1 hour at 50-55° C. is followed by cooling, dilution with 200 ml of methanol, filtration and dropwise addition to a solution of 24 g of sodium hydroxide in 500 ml of ice-water. Filtering with suction is followed by washing with water until neutral and drying at 50° C. in vacuo. The crude product is briefly brought to the boil in 50 ml of ethanol in the presence of 2 ml of triethylamine, which is followed by stirring until cold, filtering with suction, washing with ethanol and drying in vacuo: 19.4 g (80%) of a grey powder having a melting point of 140° C. and the formula

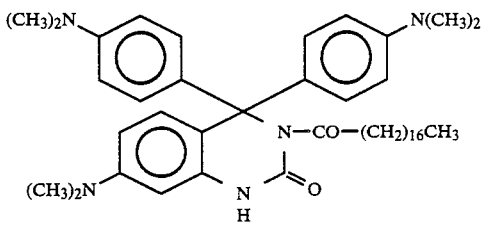

A solution in glacial acetic acid turns a blue colour with $\lambda_{max}=608$ nm. A deep blue colour develops on acid clay and in thermoprinting with bisphenol A.

The compound used as starting material, namely N-(3-dimethylamino)-N'-stearoylurea, is prepared analagously to Example 1. It is obtained in a 40% yield as a pale yellow powder having a melting point of 80–81° C.

A procedure analogous to that of Examples 1 or 2 is used to prepare the following dihydroquinazolones:

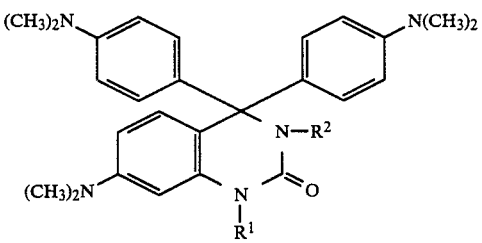

| Example | $R^1$ | $R^2$ | Colour on acid clay or with bisphenol A | $\lambda_{max}$ in nm |
|---|---|---|---|---|
| 3 | H | —CO—C(CH3)3 | blue | 605 |
| 4 | CH3 | —CO—CH—(CH3)2—CH3<br>    \|<br>    CH2CH3 | turquoise | 618 |
| 5 | CH2CH2CN | —CO—⟨C6H3⟩(Cl)(NO2) | turquoise | 617 |
| 6 | H | —CN | blue | 604 |
| 7 | H | —CO—(CH2)10CH3 | blue | 608 |
| 8 | —CH2—⟨C6H5⟩ | —CO—N(C2H5)2 | turquoise | 619 |
| 9 | —⟨C6H5⟩ | —CO—⟨C6H5⟩ | turquoise | 615 |

-continued

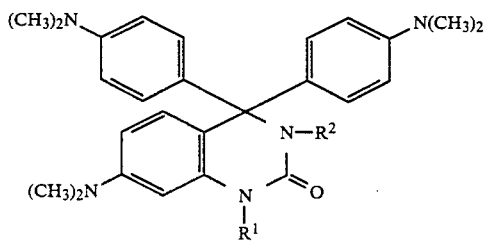

| Example | R¹ | R² | Colour on acid clay or with bisphenol A | $\lambda_{max}$ in nm |
|---|---|---|---|---|
| 10 | H | −CO−(3-pyridyl) | blue | 605 |
| 11 | H | $-\overset{S}{\underset{\parallel}{C}}-CH_3$ | blue | 607 |
| 12 | H | −CO−CF₃ | blue | 604 |
| 13 | H | −CO−(3-cyanophenyl) | blue | 605 |
| 14 | H | −CO−(1-naphthyl) | blue | 608 |
| 15 | H | −CO−(2-quinolyl) | blue | 606 |

EXAMPLE 16

270 g of Michler's hydrol and 137 g of 3-methoxy-4-methylaniline are refluxed in 1 l of methanol and 5 ml of concentrated hydrochloric acid for 2 h. Cooling down is followed by filtering with suction and recrystallisation from toluene. The result obtained is 230 g (59% of theory) of a beige crystallisate having a melting point of 190–192° C. and the formula

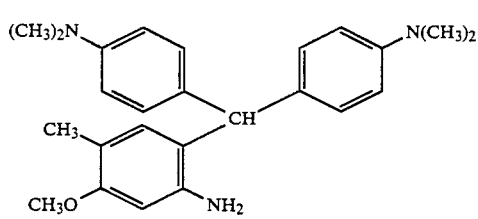

77.8 g thereof are dissolved in 400 ml of water and 57 ml of concentrated hydrochloric acid. A solution of 26 g of sodium cyanate in 200 ml of water is added dropwise at 5–10° C. in the course of 1.5 h. The mixture is subsequently stirred at room temperature for 3 h, while the formation of a precipitate is prevented by addition of 10% strength hydrochloric acid. Adjustment to pH = 8–9 with sodium hydroxide solution is followed by filtering with suction and drying. Recrystallisation from acetone produces 74.8 g (87% of theory) of a colourless crystallisate having a melting point of 221–222° C. and the formula

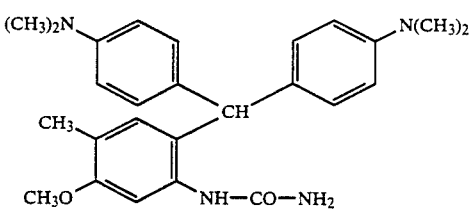

To 43.2 g of this urea in 100 ml of ethylene chloride are added at 60° C. 33.3 g of stearoyl chloride, and the mixture is then refluxed for 4 h. The solvent is drawn off and the residue is recrystallised from ethanol: 53.6 g (77% of theory) of a pale green crystalline powder having a melting point of 92–93° C. and the formula

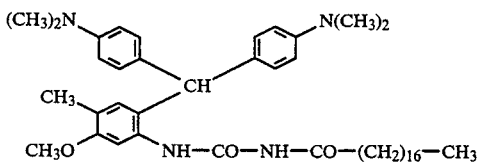

35 g of this leuco compound are dissolved at 50° C. in 4ml of dimethylformamide, and 12.3 g of chloranil are added. Stirring at 50° C. for 2 h is followed by cooling down, addition of 200 ml of methanol and filtration. The green filtrate is added dropwise to a solution of 8 g of sodium hydroxide in 500 ml of ice-water, the mixture is stirred for 2 h and then filtered with suction, and the filter residue is washed until neutral and dried. This is followed by brief boiling in 50 ml of ethanol in the presence of 1 ml of triethylamine, cooling down and filtration with suction. The result obtained is 12.5 g (36% of theory) of a colourless crystalline powder having a melting point of 178° C. and the formula

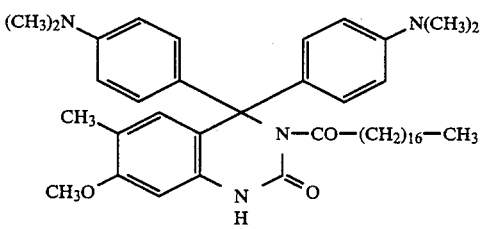

A solution in glacial acetic acid turns bluish green with $\lambda_{max}$=470,622 nm. A deep bluish green colour is obtained on acid clay and in thermoprinting with bisphenol A.

Use of the appropriate acid chlorides leads to Example 17-20 being obtained.

in 250 ml of methanol, 1.5 ml of concentrated hydrochloric acid and 30 ml of water for 5 h. The mixture is stirred until cold and is filtered with suction, and the filter residue is washed with methanol and is dried at 40° C. in vacuo: 53.3 g (57%) of a beige crystallisate having a melting point of 135-137° C. and the formula

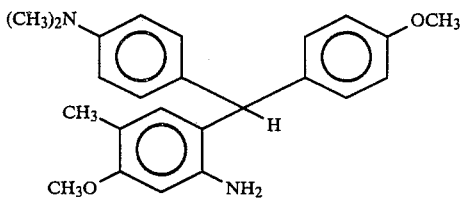

37.7 g thereof are dissolved at 0-5° C. in 200 ml of water in the presence of 30 ml of concentrated hydrochloric acid. To this solution is added dropwise and at this temperature a warm solution of 16.3 g of sodium cyanate in 200 ml of water. Hydrochloric acid is added to maintain the pH below 2. The mixture is filtered with suction, and the filter residue is washed with ice-water and dried. Recrystallisation from carbon tetrachloride gives 32.4 g (77%) of a beige crystallisate having a melting point of 180-182° C. and the formula

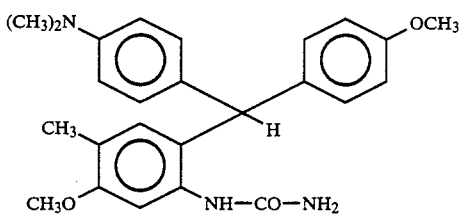

31.5 g of this urea in 75 ml of pyridine have gradually added to them at 60° C. 25.8 g of stearoyl chloride.

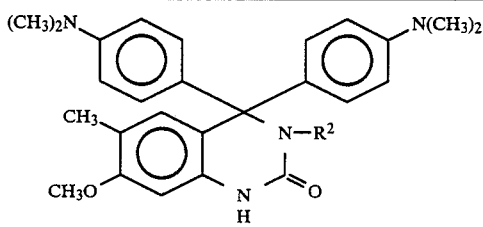

| Example | $R^2$ | Melting point | $\lambda_{max}$ nm | Colour on acid clay or with bisphenol A |
|---|---|---|---|---|
| 17 | —CO—⟨C$_6$H$_4$⟩—Cl | 256–258° C. (decomposition) | 472,622 | bluish green |
| 18 | —COC(CH$_3$)$_3$ | 207° C. | 462,622 | bluish green |
| 19 | —COCH—(CH$_2$)$_3$—CH$_3$<br>               \|<br>             CH$_2$CH$_3$ | 237° C. (decomposition) | 474,622 | bluish green |
| 20 | —CO(CH$_2$)$_{10}$—CH$_3$ | 170–171° C. | 472,622 | bluish green |

EXAMPLE 21

34.3 g of 3-methoxy-4-methylaniline and 64.3 g of 4-(dimethylamino)-4′-methoxybenzohydrol are refluxed Cooling down is followed by discharge into 700 ml of ice-water, the resulting mixture being brought to pH 3.5 with hydrochloric acid. The mixture is stirred overnight and then filtered with suction, and the filter residue is washed with water and dried in vacuo. Recrystallisation from ethanol gives 34.4 g (67%) of a pale pink crystallisate having a melting point of 79-81° C. and the formula

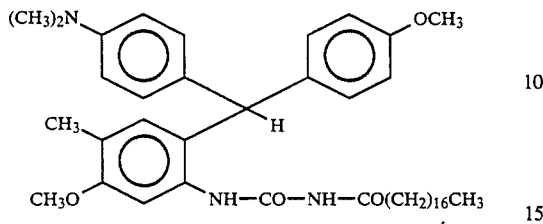

To 34.3 g of this leuco compound in 50 ml of dimethylformamide are added, at 60° C., 12.3 g of chloranil. After 1 h at 65-70° C., the mixture is cooled down, is diluted with 200 ml of methanol and is added dropwise to a solution of 16 g of sodium hydroxide in 700 ml of water. The suspension is filtered off with suction, is washed with 450 ml of methanol/water (1:2) and 100 ml of water until neutral and is dried in vacuo. The crude product is boiled up in ethanol, is stirred until cold, is filtered off with suction, is washed with ethanol and is dried in vacuo. This gives 17.1 g (50% of theory) of a pale pink crystalline powder having a melting point of 120-122° C. and the formula

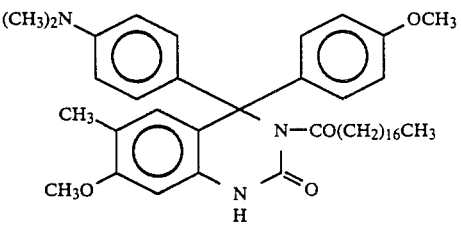

A solution in glacial acetic acid turns deeply claret with $\lambda_{max}=380, 450, 525, 542$ nm.

A deep claret colour is likewise obtained on acid clay and with bisphenol A.

The following examples are obtained analogously:

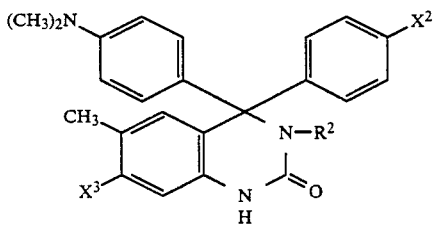

| Example | $X^2$ | $X^3$ | $R^2$ | Colour on acid clay with bisphenol A |
|---|---|---|---|---|
| 22 | $(CH_3)_2N$ | $CH_3O$ | −CO−(2,5-dichlorophenyl) | bluish green |
| 23 | $(CH_3)_2N$ | $C_{18}H_{37}O$ | −CO−phenyl | bluish green |
| 24 | $CH_3O$ | $NHC_2H_5$ | −CO−(4-pyridyl) | green |
| 25 | pyrrolidin-1-yl | H | $-CO-CH(CH_2)_3CH_3$ with $CH_2CH_3$ | yellowish green |
| 26 | −NH−(2,2,6,6-tetramethyl-1-methylpiperidin-4-yl) | $-C_4H_9$ | −CO−(4-methylsulfonylphenyl) | green |

-continued

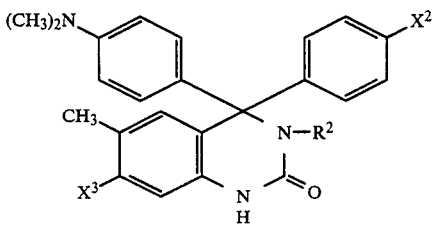

| Example | X² | X³ | R² | Colour on acid clay with bisphenol A |
|---------|-----|-----|-----|-----|
| 27 | (C₂H₅)₂N | Cl | —CO—(benzoxazol-5-yl) | green |
| 28 | (C₄H₉)₂N | —NH—CO—(CH₂)₁₀CH₃ | —SO₂—(3,4-dichlorophenyl) | green |

EXAMPLE 29

68.6 g of 3-methoxy-4-methylaniline and 129 g of 4-dimethylamino-4'-methoxybenzohydrol are refluxed under nitrogen in 500 ml of methanol, 60 ml of water and 8 ml of concentrated hydrochloric acid for 4 h. Cooling down is followed by filtration with suction, washing with methanol and drying. Recrystallisation from methylcyclohexane gives 99 g (53% of theory) of a colourless crystallisate having a melting point 136–137° C. and the formula

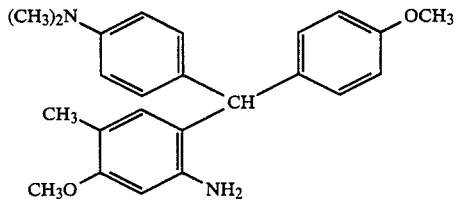

To 37.7 g of this amino compound in 100 ml of anhydrous toluene is added at 50° C. under nitrogen a solution of 19.6 g of benzenesulphonyl isocyanate in 45 ml of anhydrous toluene in the course of 30 min. The mixture is stirred at 50–60° C. for 1 h and is cooled down, 5 ml of ethanol are added, and the solids are filtered off with suction. This gives 36 g (92% of theory) of pink crystalline powder having a melting point of 198–200° C. and the formula

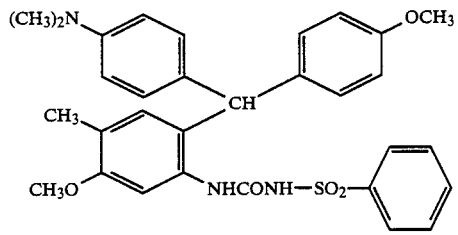

To 16.8 g of this leuco compound in 20 ml of dimethylformamide are added at 60° C. 7.4 g of chloranil. After 1 h at 60° C. the mixture is cooled down, 20 ml of glacial acetic acid are added, and the resulting mixture is poured on to 300 ml of ice-water. The red suspension is brought to pH=9–10 with 130 ml of 2.5-molar sodium hydroxide solution and is filtered with suction. The filter residue is washed until neutral and dried. It is then chromatographed over 600 ml of silica gel and eluated with about 1.5 l of chloroform/ethyl acetate 1:1. After the solvent has been drawn off, the residue is taken up in 35 ml of ethyl acetate, 1 ml of triethylamine is added, and the mixture is stirred for 1 h. Filtration with suction, washing with ethyl acetate and drying give 14.2 g (85% of theory) of a slightly beige crystalline powder having a melting point of 174° C. and the formula

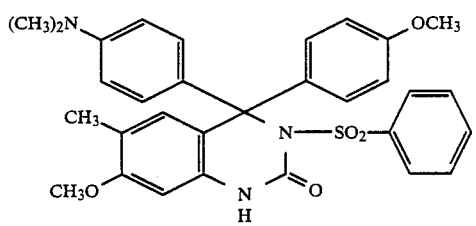

A solution in glacial acetic acid turns deep claret with $\lambda_{max}=546$ nm.

A deep red colour is likewise obtained on acid clay and in thermoprinting with bisphenol A.

The compounds of Examples 30–41 can be obtained analogously:

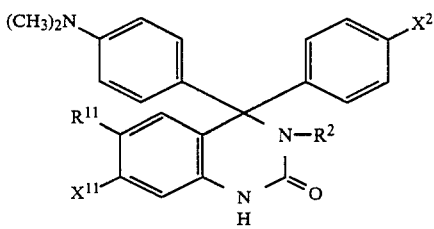

| Example | $X^2$ | $X^{11}$ | $R^{11}$ | $R^2$ | Colour on acid clay or with bisphenol A |
|---|---|---|---|---|---|
| 30 | $CH_3O$ | $CH_3O$ | $C_4H_9$ | $-SO_2-C_6H_4-CH_3$ | claret |
| 31 | $C_2H_5O$ | $CH_3O$ | $CH_3$ | $-SO_2-C_6H_4-C_{12}H_{25}$ | claret |
| 32 | Cl | $C_3H_7$ | $CH_3$ | $-SO_2-C_6H_3(NO_2)(Cl)$ | yellow |
| 33 | H | $N(C_2H_5)_2$ | Cl | $-SO_2-C_6H_2(Cl)_2(OCH_3)$ | green |
| 34 | H | $C_6H_5CH_2O$ | $CH_3O$ | $-SO_2CF_3$ | red |
| 35 | $CH_3$ | $N(CH_3)_2$ | $CH_3$ | $-SO_2-C_6H_4-OCH_3$ | green |
| 36 | $CH_3O$ | H | $Cl-C_6H_4-N(CH_3)-$ | $-SO_2CH_3$ | red |
| 37 | $C_{18}H_{37}O$ | $C_2H_5O$ | Cl | $-SO_2-C_6H_4-CH_3$ | bluish red |
| 38 | $C_6H_5CH_2$ | $C_4H_9CONH$ | $CH_3$ | $-SO_2-O-C_6H_5$ | yellow |
| 39 | $C_2H_5$ | $C_{12}H_{25}O$ | Cl | $-SO_2-N(CH_3)(C_6H_5)$ | red |
| 40 | $OCH_3$ | $CH_3S$ | $CH_3$ | $-C(O)-O-C_6H_4-Cl$ | green |

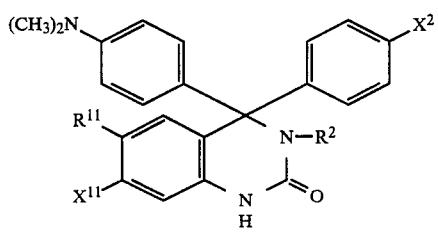

| Example | X² | X¹¹ | R¹¹ | R² | Colour on acid clay or with bisphenol A |
|---|---|---|---|---|---|
| 41 | C₆H₅CH₂O | NHCONHCON⟨C₅H₁₀⟩ | CH₃ | −C(=O)−N⟨C₅H₁₀⟩ | red |

EXAMPLE 42

40.5 g of Michler's hydrol and 26.9 g of 3-dimethylaminophenylurea are refluxed under nitrogen in 150 ml of ethanol and 2 ml of glacial acetic acid for 2 h. The mixture is cooled down and filtered with suction, the filter residue is dried: 30.6 g (47% of theory) of a beige crystallisate of the formula

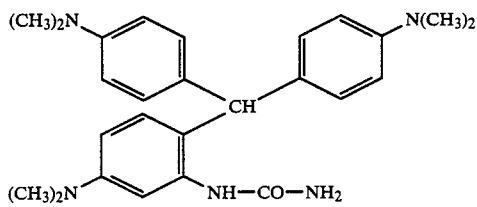

melting point from carbon tetrachloride: 118–120° C.

21.5 g of this urea are suspended at 50–60° C. under nitrogen in 50 ml of pyridine. To this suspension are added dropwise 8.2 g of 2-ethylhexanoyl chloride in the course of 15 min. The resulting solution is cooled down and poured on to 500 ml of ice-water, and the solids are filtered off with suction and washed with water. The solids obtained are then stirred in 100 ml of ethanol for 2 days and filtered off with suction. Recrystallisation from ethanol gives 6.7 g (24% of theory) of a beige crystallisate having a melting point of 203° C. and the formula

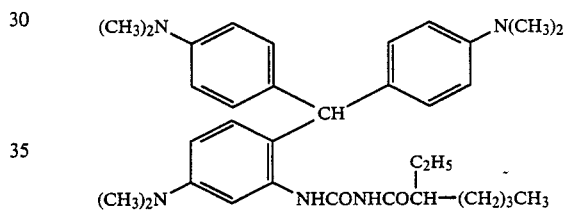

To 5.6 g of this leuco compound in 10 ml of dimethylformamide are added at 60° C. 2.46 g of chloranil, and the temperature is maintained for 1 h. Cooling down is followed by dilution with 40 ml of methanol, filtration and discharge on to a solution of 3 g of sodium hydroxide in 250 ml of ice-water. The suspension is filtered with suction and is washed with 120 ml of methanol/water 1:2 and water until neutral. The filter residue, while still moist, is boiled up in 20 ml of ethanol and 3 ml of 10% strength sodium hydroxide solution. Cooling down is followed by filtration with suction, washing with ethanol and drying. This gives 5.4 g (97% of theory) of a grey powder of melting point 226–227° C. and the formula

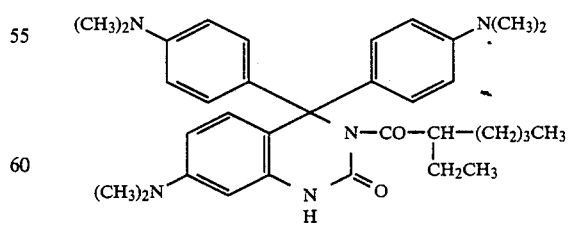

A solution in glacial acetic acid turns deep blue with $\lambda_{max} = 606$ nm.

A deep blue colour is likewise obtained on acid clay and in thermoprinting with bisphenol A.

Examples 43–51 are obtained analogously:

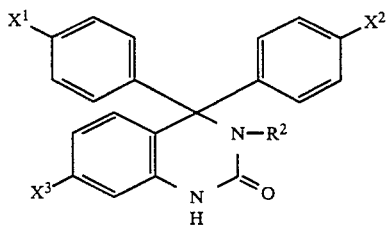

| Example | $X^1$ | $X^2$ | $X^3$ | $R^2$ | Colour on acid clay with bisphenol A |
|---|---|---|---|---|---|
| 43 | $N(CH_3)_2$ | $N(CH_3)_2$ | $N(CH_3)_2$ | $-CO-\text{C}_6\text{H}_4-CH_3$ | blue |
| 44 | $N(CH_3)_2$ | $N(CH_3)_2$ | $N(C_2H_5)_2$ | $-CO-\text{C}_6\text{H}_4-COO(CH_2)_5CH_3$ | blue |
| 45 | morpholino | $OCH_3$ | $N(CH_3)_2$ | $-S(O)-C_6H_5$ | yellowish green |
| 46 | $C_6H_5N(CH_3)-$ | $OCH_3$ | $N(CH_2-C_6H_5)_2$ | $-CO-(2\text{-pyridyl})$ | yellowish green |
| 47 | $NC-C_6H_4-N(CH_3)-$ | $OCH_3$ | $N(CH_3)_2$ | $-CO-CH_2-(4\text{-pyridyl})$ | blackish blue |
| 48 | $N(CH_3)_2$ | $N(CH_3)_2$ | $N(CH_3)(CH_2CH_2CN)$ | $-CO-(5\text{-methoxy-1,3-dimethylindolyl})$ | blue |
| 49 | $N(C_2H_5)_2$ | Cl | $N(CH_2CH_2OCOCH_3)_2$ | $-COCF_3$ | yellowish green |
| 50 | $N(CH_3)_2$ | $N(CH_3)_2$ | $-N=N-C(CH_3)(C_6H_5)-CH(CH_3)-CH(C_6H_5)-$ | $-COC_{17}H_{35}$ | green |
| 51 | $C_6H_5NH-$ | $SCH_3$ | $N(CH_2CH_2OCH_3)_2$ | $-CO-C_6H_4-NO_2$ | green |

EXAMPLE 52

25.7 g of 4-dimethylamino-4'-methoxybenzohydrol and 44.6 g of N-(3-dimethylaminophenyl)-N'-stearoylurea are refluxed under nitrogen in 140 ml of ethanol in the presence of 3 ml of glacial acetic acid and 0.7 ml of concentrated hydrochloric acid for 2 h. The solution is then cooled down and filtered with suction. This gives 62.2 g (91% of theory) of a pale green crystallisate having a melting point of 104° C. and the formula

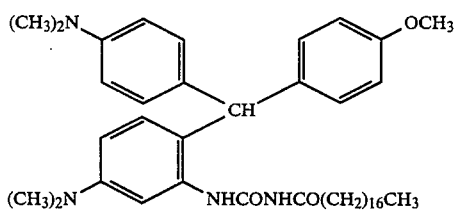

To 27.4 g of this leuco compound in 60 ml of ethanol are added at 60° C. 9.84 g of chloranil, and the mixture is stirred at this temperature for 4 h. Cooling down is followed by taking up in 150 ml of methanol, filtration and discharge on to a solution of 8 g of NaOH in 750 ml of ice-water. The solids are then filtered off with suction, washed with water until neutral and stirred into 50 ml of ethanol while still moist. This mixture is discharged on to 100 ml of water, and the solids are filtered off with suction and washed with water. Drying leaves 19.5 g (75% of theory) of a beige powder having a melting point of 91–95° C. and the formula

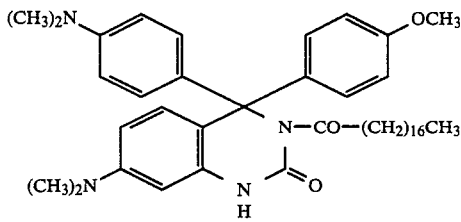

A solution in glacial acetic acid turns deep green with $\lambda_{max}=474{,}621$ nm.

A deep yellowish green colour is likewise obtained on acid clay and in thermoprinting with bisphenol A.

The following examples can be prepared analogously:

EXAMPLE 57

A mixture of 5.36 g of Michler's ketone and 8.90 g of N-(3-dimethylaminophenyl)-N'-stearoylurea is added with ice cooling to 15.3 g of phosphorus oxychloride and 5.67 g of phosphorus pentoxide. The mixture is then stirred at 20° C. for 26 h and at 35° C. for 34 h. The viscous melt is discharged on to 200 g of ice. The mixture is brought to pH 9 with sodium hydroxide solution and filtered with suction, and the filter residue is washed until neutral. The bluish product is boiled up three times with 40 ml of ethanol, is stirred each time until cold, and is filtered off with suction. This gives 4.45 g (32% of theory) of the compound of Example 2.

EXAMPLE 58

Preparation of a pressure-sensitive copying paper

A solution of 3 g of the 4,4-diaryldihydroquinazolone compound of Example 2 in 80 g of diisopropylnaphthalene and 17 g of kerosene is microencapsulated by coacervation using gelatin and gum arabic in a manner known per se, the microcapsules are mixed with starch solution, and the mixture is brushed on to a sheet of paper. A second sheet of paper is coated on the front with acid-activated bentonite as a colour developer. The first sheet and the sheet coated with the colour developer are laid on top of each other with the coated sides adjacent to each other. On writing on the first sheet by hand or by means of a typewriter a pressure is exerted, and a deep blue copy of excellent light fastness develops on the sheet coated with the developer.

EXAMPLE 59

1 g of the 4,4-diaryldihydroquinazoline compound of Example 16 is dissolved in 17 g of toluene. To this solution are added with stirring 12 g of polyvinyl acetate, 8 g of calcium carbonate and 2 g of titanium dioxide. The resulting suspension is diluted with toluene in a weight ratio of 1:1 and is coated with a 10 μm doctor blade on to a sheet of paper. This sheet of paper is covered with

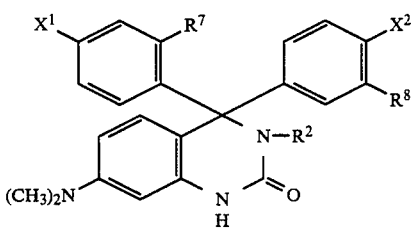

| Example | $X^1$ | $R^7$ | $X^2$ | $R^8$ | $R^2$ | Colour on acid clay with bisphenol A |
|---------|-------|-------|-------|-------|-------|--------------------------------------|
| 53 | N(CH₃)₂ | H | —N(CH₃)—C(CH₃)₂—CH₂—CH(CH₃)— | | —CO—C₆H₅ | blue |
| 54 | N(CH₃)₂ | OCH₃ | CH₃O | H | —COC(CH₃)₃ | green |
| 55 | CH₃O | H | CH₃O | CH₃O | —SO₂—C₆H₄—Cl | bluish red |
| 56 | N(C₂H₅)₂ | H | H | CH₃ | —CO—C₃H₇ | green | a second sheet of paper whose underside has been coated, in an add-on weight of 3 g/m² with a mixture consisting of 1 part of an amide wax, 1 part of a stearin wax and 1 part of zinc chloride. Through writing on the top sheet by hand or by means of a typewriter a pressure is exerted, and a deep and light-fast green colour develops on the sheet coated with the colour former.

EXAMPLE 60

The procedure of Example 58 is repeated, except that this is made of a mixture of 1.5 g of the compound of Example 52 and 1.5 g of the compound of Example 21. This gives a coloured sheet which produces a black copy which has excellent light fastness.

Preparation of heat-sensitive recording materials

EXAMPLE 61

32 g of 4,4'-isopropylidenediphenol (bisphenol A), 3.8 g of distearylamide of ethylenediamine, 89 g of kaolin, 20 g of a polyvinyl alcohol hydrolysed to 88% and 55 ml of water are ball-milled until the particle size is about 5 μm. In a separate ball mill, 6 g of the 4,4-diaryldihydroquinazolone compound of Example 1, 3 g of a polyvinyl alcohol hydrolysed to 88% and 60 ml of water are ball-milled until the particle size is about 3 μm. The two dispersions are added together, and the mixture is coated in a dry add-on weight of 5.5 g /m² on to a sheet of paper. On contacting the paper with a heated ballpoint pen the result obtained is a deep blue colour of excellent light and sublimation fastness.

EXAMPLE 62

2.7 g of the 4,4-diaryldihydroquinazolone compound of Example 29, 24 g of N-phenyl-N'-(1-hydroxy-2,2,2-trichloroethyl)-urea, 16 g of stearamide, 59 g of a polyvinyl alcohol hydrolysed to 88% and 58 ml of water are ball-milled until the particle size is 2–5 μm. This suspension is coated in a dry add-on weight of 5.5 g/m² on to a sheet of paper. On contacting the paper with a heated ballpoint pen the result obtained is a deep and light-fast claret colour.

We claim:

1. A chromogenic quinazolone of the formula

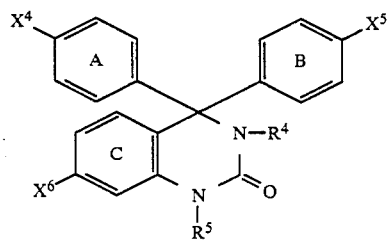

wherein
one of the radicals $X^4$, $X^5$ or $X^6$ stands for $NY^4Y^5$, $OY^6$ or $SY^6$, and the others, independently of each other, denote hydrogen, halogen, $C_1$–$C_{18}$-alkyl, optionally chlorine- and/or $C_1$ to $C_{12}$-alkyl substituted phenyl, $C_1$- to $C_{12}$-alkanoylamino, optionally chlorine- and/or $C_1$- to $C_{12}$-alkyl substituted benzoylamino, optionally $C_1$- to $C_4$-alkyl-, $C_1$- to $C_4$-alkoxy-, chlorine- or phenyl-substituted indolyl or piperidyl radicals, $NY^{4'}Y^{5'}$, $OY^{6'}$, or $SY^{6'}$, $R^3$ denotes hydrogen, $C_1$- to $C_{18}$-alkyl, cyclohexyl or optionally chlorine- and/or $C_1$- to $C_{18}$-alkyl-substituted benzyl or phenyl radicals, $R^4$ denotes a radical of the formulae

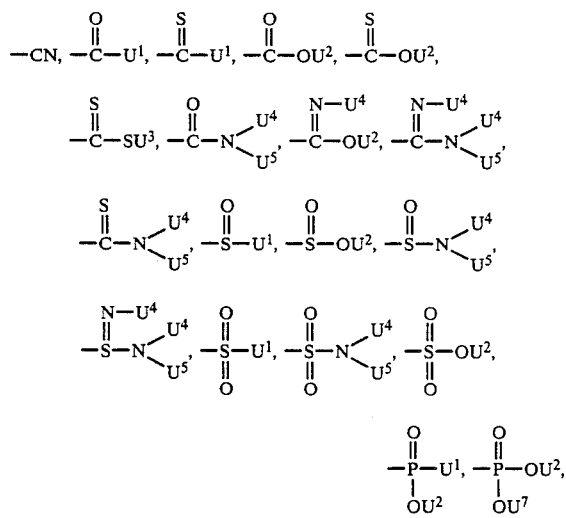

$U^1$ to $U^7$ denote hydrogen, optionally fluorine-, chlorine-, cyano-, $C_1$- to $C_4$-alkoxycarbonyl- and/or $C_1$- to $C_4$-alkoxy-substituted $C_1$- to $C_{30}$alkyl, optionally chlorine-and/or $C_1$- to $C_{18}$-alkyl-substituted cyclohexyl, optionally chlorine-, bromine-, nitro-, $C_1$- to $C_{18}$-alkyl, $C_1$- to $C_{18}$-alkoxy, $C_1$- to $C_{18}$-alkylthio, $C_1$- to $C_{18}$-monoalkylamino- or -dialkylamino-, $C_1$- to $C_{18}$-alkylsulphonyl-, cyano- and/or $C_1$- to $C_{18}$-alkoxycarbonyl substituted phenyl, benzyl, naphthyl, picolyl, pyridyl, quinolyl, pyrimidyl, pyrazinyl, triazinyl, triazolyl, thiadiazolyl, tetrazolyl, indolyl, optionally benzofused imidazole, oxazole or thiazole radicals, $Y^4$, $Y^5$ and $Y^6$, denote members which, together with N to which they are bonded and one of the rings A, B or C, are necessary for completing a ring system of the following formulae

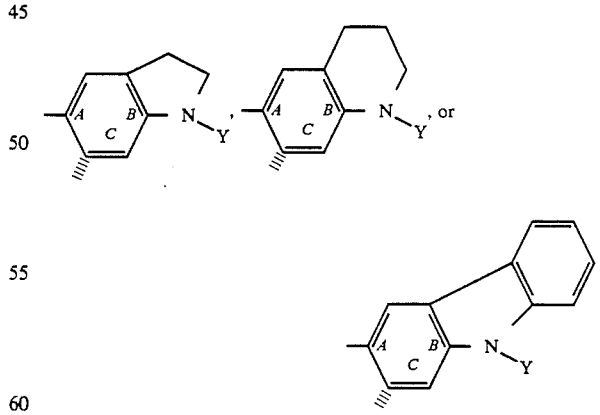

wherein
the broken line denotes the further fusion in the case of ring C,
Y stands for hydrogen, $C_1$- to $C_{18}$-alkyl which is unsubstituted or substituted by chlorine, cyano, $C_1$- to $C_4$-alkoxycarbonyl or $C_1$- to $C_4$-alkoxy, cyclohexyl, phenyl or benzyl, each of which can be substituted by chlorine, $C_1$- to $C_{12}$-alkyl or $C_1$- to $C_{12}$-alkoxy, the saturated ring moiety can carry up to 4 radicals from the group consisting of chlorine, $C_1$- to $C_4$-alkyl, $C_1$- to $C_4$-alkoxy or phenyl, $Y^{4'}$, $Y^{5'}$ and $Y^{6'}$, denote hydrogen, optionally chlorine-, cyano-, $C_1$- to $C_4$-alkoxycarbonyl- or $C_1$- to $C_4$-alkoxy-substituted $C_1$- to $C_{18}$-alkyl, cyclohexyl or phenyl or benzyl, each of which can be substituted by chlorine, $C_1$- to $C_{12}$-alkyl or $C_1$- to $C_{12}$-alkoxy, $C_1$- to $C_4$-alkyl-substituted piperidyl or have the meaning of $Y^4$, $Y^5$ or $Y^6$ respectively, or $NY^{4'}Y^{5'}$ denotes an unsubstituted or chlorine-, $C_1$- to $C_4$-alkyl- or phenyl- substituted pyrrolo, pyrrolidino, piperidino, pipecolino, morpholino, pyrazolo or pyrazolino radical, and the rings A, B and C are unsubstituted or substituted by chlorine, $C_1$- to $C_4$-alkyl, $C_1$- to $C_4$-alkoxy, unsubstituted or substituted chlorine-, $C_1$- to $C_4$-alkyl or $C_1$- to $C_4$-alkoxy-substituted phenoxy or phenylamino and-/or $C_1$- to $C_4$-alkanoylamino.

2. A chromogenic 4,4-diaryldihydroquinazolone according to claim 1, wherein $NY^4Y^5$ denotes phenyl-substituted pyrrolo, pyrrolidino, piperidino, pipecolino, morpholino, pyrazolo or a pyrazolino radical.

3. A chromogenic 4,4-diaryldihydroquinazolone of the formula

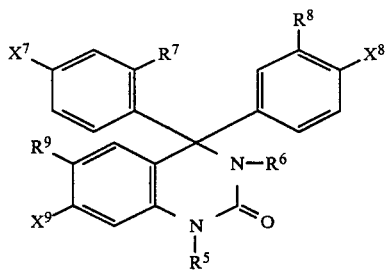

wherein
one of the radicals $X^7$, $X^8$ and $X^9$ stands for $NY^7Y^8$ and the others, independently of each other denote hydrogen, chlorine, bromine, $C_1$- to $C_{18}$-alkyl, unsubstituted phenyl or phenyl substituted by chlorine- and/or $C_1$- to $C_4$-alkyl-substituted phenyl, $C_1$- to $C_4$-alkylamino, unsubstituted benzoylamino or benzoylamino substituted by chlorine- and/or $C_1$- to $C_4$-alkyl-substituted benzolyamino, optionally methyl-, ethyl-, methoxy-, chlorine- or phenyl-substituted indolyl or piperidyl radicals, $NY^{7'}Y^{8'}$, $OY^{9'}$ or $SY^{9'}$, $R^5$ denotes hydrogen, $C_1$- to $C_4$-alkyl, cyclohexyl or phenyl, $R^6$ denotes

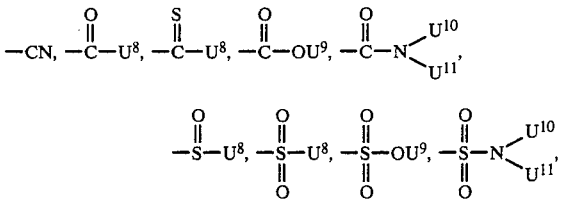

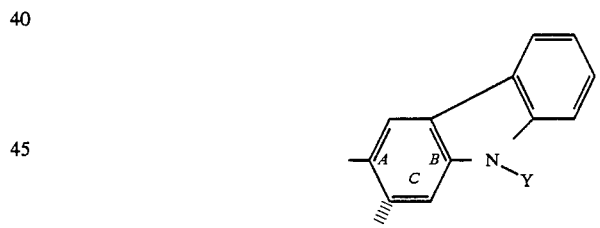

$U^8$–$U^{11}$ denote hydrogen, optionally fluorine-, chlorine- or $C_1$- to $C_4$-alkoxy-substituted $C_1$- to $C_{18}$-alkyl, cyclohexyl, unsubstituted benzyl or benzyl substituted by chlorine- and/or $C_1$- to $C_8$-alkyl, optionally chlorine-, bromine-, nitro-, $C_1$- to $C_{18}$-alkyl, $C_1$- to $C_{18}$-alkoxy, $C_1$- to $C_{18}$-alkylthio, $C_1$- to $C_{18}$-dialkyl-amino, $C_1$- to $C_{18}$-alkylsulphonyl, cyano- and/or $C_1$- to $C_{18}$-alkoxycarbonyl-substituted phenyl, naphthyl, picolyl, pyridyl, quinolyl, pyrimidyl, pyrazinyl, triazinyl, triazolyl, thiadiazolyl, tetrazolyl, indolyl, imidazole or benzo-fused imidazole, oxazole or thiazole radicals, $R^7$, $R^8$ and $R^9$, independently of one another, denote hydrogen, chlorine, bromine, $C_1$- to $C_4$-alkyl, $C_1$- to $C_4$-alkoxy, $C_1$- to $C_4$-alkylthio, amino or $C_1$- to $C_4$-alkylamino, $C_1$- to $C_4$-monoalkyl-amino or -dialkylamino, optionally methyl-, methoxy-, ethoxy- or chlorine-substituted anilino or N-$C_1$- to $C_4$-alkylanilino, $Y^7$ and $Y^8$ stands for the members which lead to the following ring systems

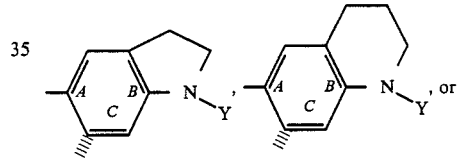

$Y^{7'}$, $Y^{8'}$ and $Y^{9'}$ denote hydrogen, chlorine-, cyano-, methoxycarbonyl-, hydroxy-, methoxy-or ethoxy-substituted $C_1$- to $C_{18}$-alkyl, cyclohexyl, benzyl or phenyl, each of which can be substituted by chlorine, methyl or methoxy, 2,2,6,6-tetramethylpiperidinyl-4-yl or 1,2,2,6,6-pentamethylpiperidinyl-4-yl or $Y^{7'}$ and $Y^{8'}$ have the meaning of $Y^7$ or $Y^8$, respectively or $NY^7Y^8$ stands for a $C_1$- to $C_4$-alkyl- and/or phenyl-substituted pyrrolidino, piperidino, morpholino or pyrazolino radical.

* * * * *

UNITED STATES PATENT AND TRADEMARK OFFICE
CERTIFICATE OF CORRECTION

PATENT NO. : 4,968,797

DATED : November 6, 1990

INVENTOR(S) : Berneth et al.

It is certified that error appears in the above-identified patent and that said Letters Patent is hereby corrected as shown below:

Col. 32, line 10  Delete "$-\overset{\overset{S}{\|}}{C}-SU^3, -\overset{\overset{O}{\|}}{C}-N\overset{U^4}{\underset{U^5}{<}}, -\overset{\overset{N-U^4}{\|}}{C}-OU^2, -\overset{\overset{N-U^4}{\|}}{C}-N\overset{U^4}{\underset{U^5}{<}}$," and substitute -- $-\overset{\overset{S}{\|}}{C}-SU^3, -\overset{\overset{O}{\|}}{C}-N\overset{U^4}{\underset{U^5}{<}}, -\overset{\overset{N-U^6}{\|}}{C}-OU^2, -\overset{\overset{N-U^6}{\|}}{C}-N\overset{U^4}{\underset{U^5}{<}}$, --

Col. 32, line 18  Delete "$-\overset{\overset{N-U^4}{\|}}{S}-N\overset{U^4}{\underset{U^5}{<}}, -\overset{\overset{O}{\|}}{\underset{\underset{O}{\|}}{S}}-U^1, -\overset{\overset{O}{\|}}{\underset{\underset{O}{\|}}{S}}-N\overset{U^4}{\underset{U^5}{<}}, -\overset{\overset{O}{\|}}{\underset{\underset{O}{\|}}{S}}-OU^2$, and sub-

UNITED STATES PATENT AND TRADEMARK OFFICE
CERTIFICATE OF CORRECTION

PATENT NO. : 4,968,797

DATED : November 6, 1990

INVENTOR(S) : Berneth et al.

It is certified that error appears in the above-identified patent and that said Letters Patent is hereby corrected as shown below:

stitute -- 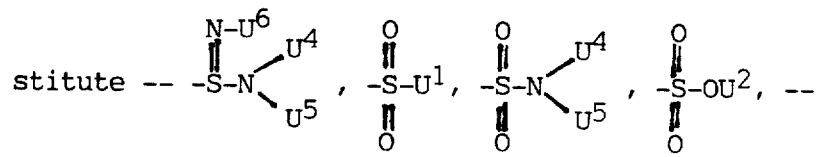 --

Signed and Sealed this

First Day of June, 1993

Attest:

*Attesting Officer*

MICHAEL K. KIRK

*Acting Commissioner of Patents and Trademarks*